United States Patent
Sunagawa et al.

(10) Patent No.: US 6,258,031 B1
(45) Date of Patent: Jul. 10, 2001

(54) ULTRASOUND DIAGNOSTIC APPARATUS

(75) Inventors: Kazuhiro Sunagawa, Sendai; Yoshinao Tannaka, Aiko-gun; Hiroshi Kanai, Sendai, all of (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/594,487

(22) Filed: Jun. 16, 2000

(30) Foreign Application Priority Data

Aug. 24, 1999 (JP) .................................................. 11-237433

(51) Int. Cl.[7] ........................................................ A61B 8/00
(52) U.S. Cl. ............................................ 600/443; 600/447
(58) Field of Search .................................. 600/437, 443, 600/442, 448, 444, 445

(56) References Cited

FOREIGN PATENT DOCUMENTS 9-313485   12/1997  (JP) .
10-5226     1/1998  (JP) .

Primary Examiner—Marvin M. Lateef
Assistant Examiner—Maulin Patel
(74) Attorney, Agent, or Firm—Louis Woo

(57) ABSTRACT

An ultrasound diagnostic apparatus includes a transmitting device having an ultrasound probe. The transmitting device operates for transmitting a ultrasound pulse beam from the ultrasound probe into a body. A receiving device includes the ultrasound probe. The receiving device operates for receiving an ultrasound echo beam caused in the body, and converting the received ultrasound echo beam into a corresponding electric echo signal via the ultrasound probe. A delay controlling device is operative for controlling an acoustic line direction of transmission and reception of the ultrasound pulse beam and the ultrasound echo beam. A phase detection device is operative for subjecting the electric echo signal to phase detection to generate a phase-detection result signal. A tissue velocity calculating device operates for calculating a velocity of a tissue in the body from the phase-detection result signal. A display device is operative for indicating the calculated velocity of the tissue. The delay controlling device is operative for changing the acoustic line direction of transmission and reception of the ultrasound pulse beam and the ultrasound echo beam with respect to a same object.

12 Claims, 7 Drawing Sheets

ULTRASOUND DIAGNOSTIC APPARATUS

BACKGROUND OF THE INVENTION

1. Field of the Invention

This invention relates to an ultrasound diagnostic apparatus designed to detect the velocity of an organ or a tissue in a body.

2. Description of the Related Art

General-purpose ultrasound diagnostic apparatuses can operate in any one of different modes such as a B mode, an M mode, an FFT Doppler mode, and a color Doppler mode. In some cases, a diagnosis on arteriosclerosis is based on an ultrasound diagnosis on a carotid artery which uses a general-purpose ultrasound diagnostic apparatus. Specifically, the ultrasound diagnosis is implemented by using shape information generated by the B mode and the M mode of operation of the apparatus, and blood velocity information provided by the FFr Doppler mode or the color Doppler mode of operation of the apparatus.

When the general-purpose ultrasound diagnostic apparatus operates in the B mode, the inside diameter of a blood vessel, the thickness of a blood vessel wall, and the conditions of a morbid protuberance can be evaluated from information provided by the apparatus. When the general-purpose ultrasound diagnostic apparatus operates in the M mode, a time-domain change of a blood vessel diameter in response to a heartbeat can be evaluated from information provided by the apparatus. When the general-purpose ultrasound diagnostic apparatus operates in the FET Doppler mode or the color Doppler mode, the rate of a blood flow in a blood-vessel strangulated portion caused by a morbid protuberance can be evaluated from information provided by the apparatus.

As previously mentioned, the conditions of a morbid protuberance can be evaluated by using the B mode of operation of the general-purpose ultrasound diagnostic apparatus. Specifically, the presence and the size of the morbid protuberance are observed via the apparatus. In addition, the brightnesses in an ultrasound-echo-based image (a B mode image or a sectional image) displayed on a monitor of the apparatus are observed. The conditions of the morbid protuberance are judged from the size information and the brightness information.

Generally, a morbid protuberance caused by a thrombus is indicated as an image portion having a low brightness. Therefore, in some cases, such a morbid protuberance fails to be found by using the B mode of operation of the general-purpose ultrasound diagnostic apparatus.

As previously mentioned, the conditions of a morbid protuberance are judged from size information and brightness information during the B mode of operation of the general-purpose ultrasound diagnostic apparatus. Since the brightness information is used, it is difficult to quantitatively evaluate the conditions of the morbid protuberance.

Japanese published unexamined patent application 9-313485 discloses an ultrasound apparatus for diagnosing the conditions of a tissue in a body which uses tissue Doppler imaging. The apparatus in Japanese application 9-313485 measures motion of the tissue relative to an ultrasound probe. Accordingly, it is difficult for the apparatus to detect a self-motionless suspended portion in a moving tissue. In addition, it is difficult for the apparatus to detect motion of a tissue in a direction perpendicular to an ultrasound beam.

Japanese published unexamined patent application 10-5226 discloses an ultrasound apparatus for diagnosing the conditions of a tissue in a body. In the apparatus of Japanese application 10-5226, information is generated which represents the amplitude and the phase of an electric signal resulting from detection of ultrasound echoes. Then, the instantaneous position of an object is decided on the basis of the amplitude and phase information in a least-squares method. Accurate tracking on the object is implemented in response to the decided instantaneous position thereof. The accurate tracking makes it possible for the apparatus to correctly detect self-motion of a portion in a tissue which is being greatly moved by a heartbeat.

The apparatus of Japanese application 9-313485 and the apparatus of Japanese application 10-5226 can detect only a component of the velocity of an object in a direction along the acoustic line of an ultrasound beam.

Some ultrasound diagnostic apparatuses for measuring a blood flow rate are equipped with arrangements which implement correction related to the angle between the direction of a blood vessel and the direction of the acoustic line of an ultrasound beam. This correction method can not be applied to detection of the velocity of an organ or a tissue which is moving in various directions.

SUMMARY OF THE INVENTION

It is an object of this invention to provide an ultrasound diagnostic apparatus which can measure the direction of motion of a tissue (or an organ) in a body, the velocity of the tissue, and the distance traveled by the tissue regardless of the angular difference between the direction of motion of the tissue and the direction of the acoustic line of an ultrasound beam.

A first aspect of this invention provides an ultrasound diagnostic apparatus comprising transmitting means including an ultrasound probe for transmitting a ultrasound pulse beam from the ultrasound probe into a body; receiving means including the ultrasound probe for receiving an ultrasound echo beam caused in the body, and converting the received ultrasound echo beam into a corresponding electric echo signal via the ultrasound probe; delay controlling means for controlling an acoustic line direction of transmission and reception of the ultrasound pulse beam and the ultrasound echo beam; phase detection means for subjecting the electric echo signal to phase detection to generate a phase-detection result signal; tissue velocity calculating means for calculating a velocity of a tissue in the body from the phase-detection result signal; and display means for indicating the calculated velocity of the tissue; wherein the delay controlling means comprises means for changing the acoustic line direction of transmission and reception of the ultrasound pulse beam and the ultrasound echo beam with respect to a same object.

A second aspect of this invention is based on the first aspect thereof, and provides an ultrasound diagnostic apparatus wherein the ultrasound probe includes transducer elements, and further comprising means for selecting ones from among the transducer elements as active elements in response to a depth of a measured portion of the tissue from a surface of the body.

A third aspect of this invention is based on the first aspect thereof, and provides an ultrasound diagnostic apparatus wherein the delay controlling means comprises means for changing the acoustic line direction of transmission and reception of the ultrasound pulse beam and the ultrasound echo beam in response to a depth of a measured portion of the tissue from a surface of the body.

A fourth aspect of this invention is based on the first aspect thereof, and provides an ultrasound diagnostic apparatus wherein the delay controlling means comprises means for changing the acoustic line direction of transmission and reception of the ultrasound pulse beam and the ultrasound echo beam among a plurality of different directions with respect to the tissue, and the tissue velocity calculating means comprises means for calculating a velocity of the tissue in a direction perpendicular to a front surface of the ultrasound probe, a distance traveled by the tissue in the direction perpendicular to the front surface of the ultrasound probe, a velocity of the tissue in a direction parallel to the front surface of the ultrasound probe, and a distance traveled by the tissue in the direction parallel to the front surface of the ultrasound probe from the phase-detection result signal.

A fifth aspect of this invention is based on the first aspect thereof, and provides an ultrasound diagnostic apparatus wherein the delay controlling means comprises means for changing the acoustic line direction of transmission and reception of the ultrasound pulse beam and the ultrasound echo beam to scan arterial walls in the body, the tissue velocity calculating means comprises means for calculating a velocity of the arterial walls in a direction of a normal, a distance traveled by the arterial walls in the direction of the normal, a velocity of the arterial walls in a direction of a tangent, and a distance traveled by the arterial walls in the direction of the tangent from the phase-detection result signal, and the display means comprises means for indicating the calculated velocity of the arterial walls in the direction of the normal, the calculated distance traveled by the arterial walls in the direction of the normal, the calculated velocity of the arterial walls in the direction of the tangent, and the calculated distance traveled by the arterial walls in the direction of the tangent as waveforms.

A sixth aspect of this invention is based on the fourth aspect thereof, and provides an ultrasound diagnostic apparatus wherein the display means comprises means for indicating a B-mode image of the body, and means for indicating the calculated velocity of the tissue in the direction perpendicular to the front surface of the ultrasound probe, the calculated distance traveled by the tissue in the direction perpendicular to the front surface of the ultrasound probe, the calculated velocity of the tissue in the direction parallel to the front surface of the ultrasound probe, and the calculated distance traveled by the tissue in the direction parallel to the front surface of the ultrasound probe as two-dimensional color distributions superimposed over the B-mode image of the body.

A seventh aspect of this invention is based on the fifth aspect thereof, and provides an ultrasound diagnostic apparatus wherein the display means comprises means for indicating a B-mode image of the body, and means for indicating the calculated velocity of the arterial walls in the direction of the normal, the calculated distance traveled by the arterial walls in the direction of the normal, the calculated velocity of the arterial walls in the direction of the tangent, and the calculated distance traveled by the arterial walls in the direction of the tangent as two-dimensional color distributions superimposed over the B-mode image of the body.

An eighth aspect of this invention is based on the sixth aspect thereof, and provides an ultrasound diagnostic apparatus wherein the display means comprises means for indicating a blood pressure waveform and an electrocardiogram superimposed over the B-mode image of the body and the two-dimensional color distributions.

A ninth aspect of this invention is based on the seventh aspect thereof, and provides an ultrasound diagnostic apparatus wherein the display means comprises means for indicating a blood pressure waveform and an electrocardiogram superimposed over the B-mode image of the body and the two-dimensional color distributions.

A tenth aspect of this invention provides an ultrasound diagnostic apparatus comprising first means for transmitting a first ultrasound pulse beam into a body toward an object within the body along a first direction; second means for receiving a first ultrasound echo beam caused by reflection of the first ultrasound pulse beam at the object and coming from the object along the first direction; third means for transmitting a second ultrasound pulse beam into the body toward the object within the body along a second direction angularly different from the first direction; fourth means for receiving a second ultrasound echo beam caused by reflection of the second ultrasound pulse beam at the object and coming from the object along the second direction; fifth means for calculating a velocity of the object along the first direction from the first ultrasound echo beam received by the second means; and sixth means for calculating a velocity of the object along the second direction from the second ultrasound echo beam received by the fourth means.

An eleventh aspect of this invention is based on the tenth aspect thereof, and provides an ultrasound diagnostic apparatus wherein the first direction is perpendicular to a surface of the body, and further comprising seventh means for calculating a velocity of the object along a third direction parallel to the surface of the body from the velocity calculated by the fifth means, the velocity calculated by the sixth means, and an angular difference between the first direction and the second direction.

A twelfth aspect of this invention is based on the tenth aspect thereof, and provides an ultrasound diagnostic apparatus further comprising seventh means for calculating a direction of motion of the object from the velocity calculated by the fifth means, the velocity calculated by the sixth means, and an angular difference between the first direction and the second direction, and eighth means for calculating a velocity of the object along the calculated direction of motion of the object from the velocity calculated by the fifth means, the velocity calculated by the sixth means, and the angular difference between the first direction and the second direction.

DESCRIPTION OF THE PREFERRED EMBODIMENT

Figure 1:
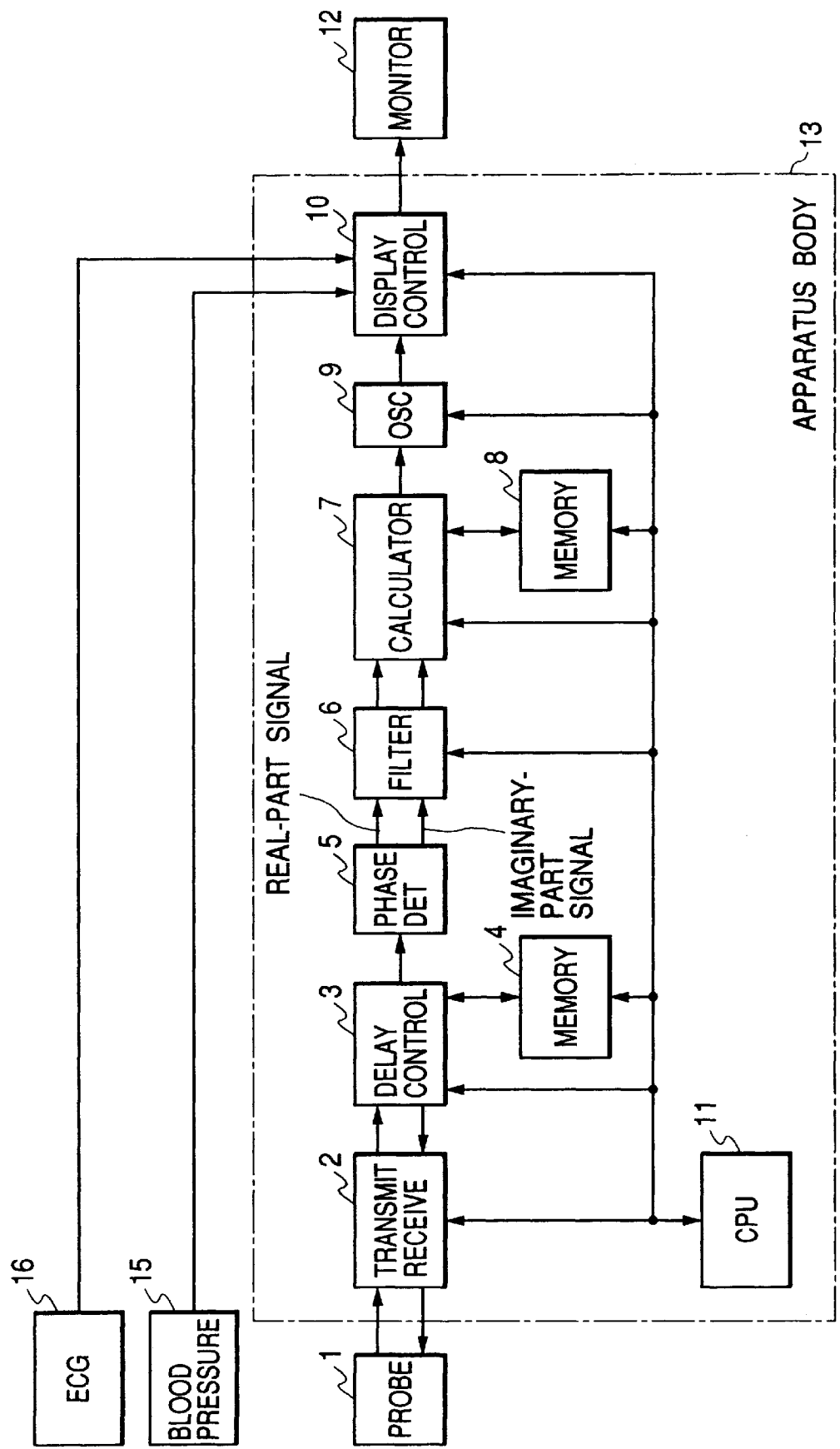
FIG. 1 is a block diagram of an ultrasound diagnostic apparatus according to an embodiment of this invention.

FIG. 1 shows an ultrasound diagnostic apparatus according to an embodiment of this invention. The apparatus of FIG. 1 includes an ultrasound probe 1, a monitor (display)

12, and an apparatus body 13. The ultrasound probe 1 and the monitor 12 are connected to the apparatus body 13. In addition, a blood pressure detector 15 and an electrocardiograph (ECG) 16 can be connected to the apparatus body 13.

The apparatus body 13 includes a transmitting/receiving section 2, a delay controller 3, a memory 4, a phase detector 5, a filter 6, a calculator 7, a memory 8, a digital scan converter (DSC) 9, a display controller 10, and a CPU 11. The transmitting/receiving section 2 is connected to the ultrasound probe 1, the delay controller 3, and the CPU 11. The delay controller 3 is connected to the memory 4, the phase detector 5, and the CPU 11. The memory 4 is connected to the CPU 11. The phase detector 5 is connected to the filter 6. The filter 6 is connected to the calculator 7 and the CPU 11. The calculator 7 is connected to the memory 8, the DSC 9, and the CPU 11. The memory 8 is connected to the CPU 11. The DSC 9 is connected to the display controller 10 and the CPU 11. The display controller 10 is connected to the CPU 11 and the monitor 12. The blood pressure detector 15 and the ECG 16 can be connected to the display controller 10.

The CPU 11 operates in accordance with a program stored in an internal memory or an external memory. According to the program, the CPU 11 controls the transmitting/receiving section 2, the delay controller 3, the memory 4, the filter 6, the calculator 7, the memory 8, the DSC 9, and the display controller 10. The CPU 11 can change operation of the apparatus among a plurality of different modes in response to user's request.

Figure 2:
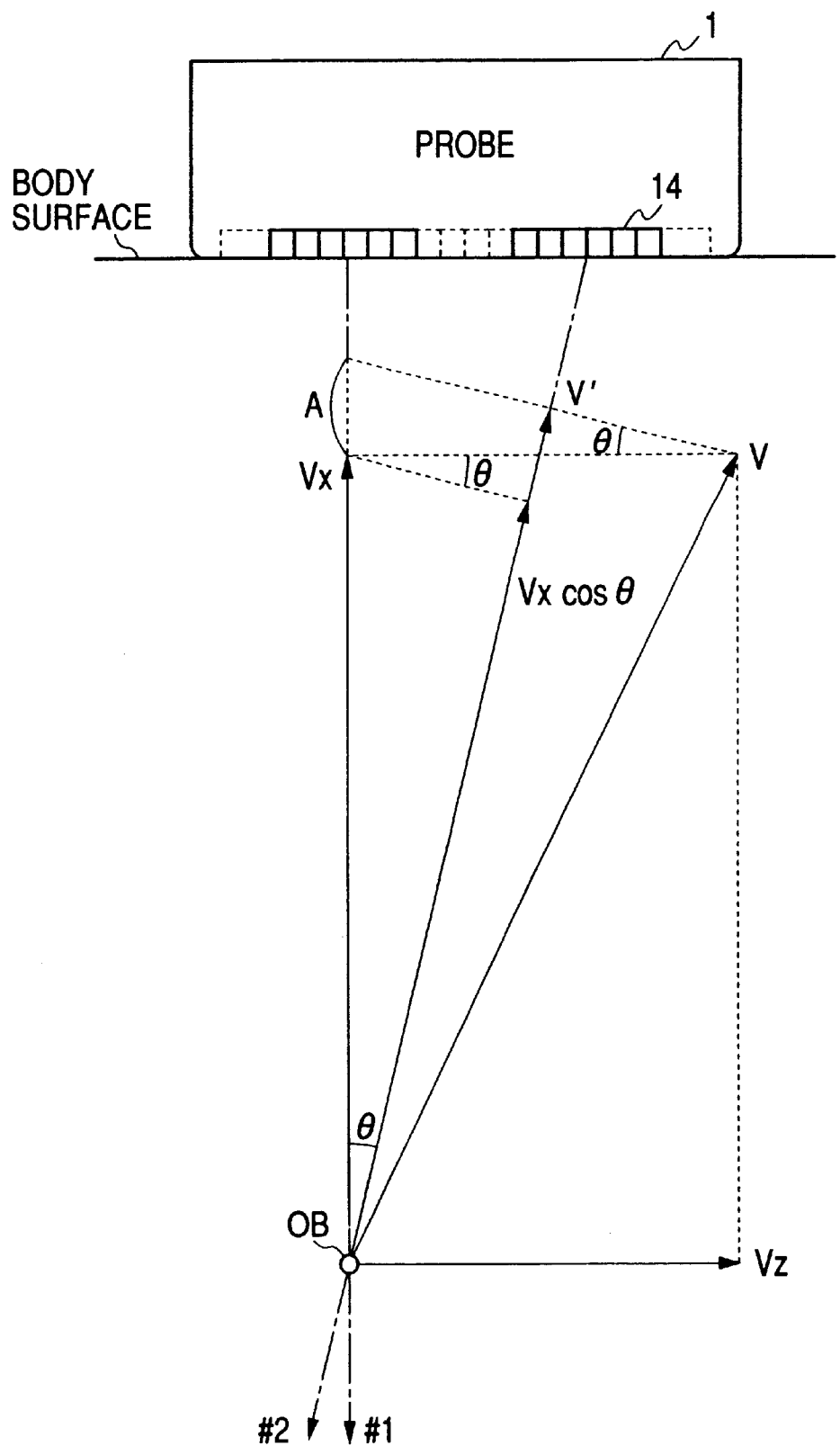
FIG. 2 is a diagram of an ultrasound probe, acoustic line directions, and an object.

As shown in FIG. 2, the ultrasound probe 1 includes an array 14 of piezoelectric elements (electric-ultrasound transducer elements). The ultrasound probe 1 is applied to the surface of a body to be examined. In this case, as shown in FIG. 2, the piezoelectric-element array 14 adjoins the body surface. The ultrasound probe 1 has a flat front surface to be in contact with the body surface. The front surface of the ultrasound probe 1 substantially coincides with a front surface of the piezoelectric-element array 14.

With reference back to FIG. 1, the transmitting/receiving section 2 generates electric drive pulse signals for the piezoelectric elements in the ultrasound probe 1 according to the control by the CPU 11. The electric drive pulse signals have a given period. The transmitting/receiving section 2 feeds the electric drive pulse signals to the piezoelectric elements in the ultrasonic probe 1. The piezoelectric element array 14 in the ultrasonic probe 1 converts the electric drive pulse signals into a beam of corresponding ultrasound pulses, and emits the ultrasound pulse beam into a body to be examined.

Under the control by the CPU 11, the delay controller 3 adjusts delays of the electric drive pulse signals applied to the piezoelectric elements in the ultrasonic probe 1 from the transmitting/receiving section 2, thereby changing the direction of the acoustic line of the emitted ultrasound pulse beam. In other words, the delay controller 3 controls the transmitting directivity of the piezoelectric element array 14 in the ultrasound probe 1. Specifically, the memory 4 stores data for transmission delay control. The delay controller 3 reads the transmission delay control data from the memory 4, and controls the delays of the electric drive pulse signals in accordance with the transmission delay control data.

The transmission delay control data in the memory 4 correspond to preset different deflection angles of the acoustic line of the emitted ultrasound pulse beam. Thus, the acoustic line of the emitted ultrasound pulse beam is changed among the preset deflection angles.

The emitted ultrasound pulse beam is reflected at various places within the body. The reflection-resultant ultrasound pulse beams are ultrasound echo beams. Portions of the ultrasound echo beams return to the piezoelectric elements in the ultrasound probe 1. The piezoelectric elements convert the received portions of the ultrasound echo beams into corresponding electric echo signals. The ultrasound probe 1 outputs the electric echo signals to the transmitting/receiving section 2.

The transmitting/receiving section 2 amplifies the electric echo signals. The transmitting/receiving section 2 outputs the amplification-resultant electric echo signals to the delay controller 3.

Under the control by the CPU 11, the delay controller 3 adjusts delays of the amplification-resultant electric echo signals, and adds or combines the delay-adjusted electric echo signals into a received echo signal being a signal (a Doppler-shift signal) having a Doppler shift or a Doppler frequency. Thereby, the delay controller changes the direction of the acoustic line of an ultrasound echo beam most sensitively received. This action of the delay controller 3 is equivalent to control of the receiving directivity of the piezoelectric element array 14 in the ultrasound probe 1. Specifically, the memory 4 stores data for reception delay control. The delay controller 3 reads the reception delay control data from the memory 4, and controls the delays of the electric echo signals in accordance with the reception delay control data. The delay controller 3 outputs the Doppler-shift signal to the phase detector 5.

The reception delay control data in the memory 4 correspond to the preset different deflection angles of the acoustic line of an ultrasound echo beam most sensitively received. Thus, the acoustic line of the ultrasound echo beam most sensitively received is changed among the preset deflection angles.

The phase detector 5 subjects the Doppler-shift signal to phase detection regarding the Doppler shift (the Doppler frequency) relative to a reference signal. The phase detection generates a real-part signal and an imaginary-part signal (a positive-polarity signal and a negative-polarity signal) in response to the Doppler-shift signal. The phase detector 5 outputs the real-part signal and the imaginary-part signal to the filter 6.

The real-part signal and the imaginary-part signal have desired echo components representing organ and tissue motions and also unwanted echo components representing blood flows and others. Under the control by the CPU 11, the filter 6 removes the unwanted echo components from the real-part signal and the imaginary-part signal while passing the desired echo components thereof. The filter 6 outputs the resultant real-part signal and the resultant imaginary-part signal to the calculator 7.

Under the control by the CPU 11, the calculator 7 computes the velocity of an object such as an organ or a tissue in the body on the basis of the output signals from the filter 6. Thus, the velocity of the object is measured. The calculator 7 generates data (velocity data) representing the computed object velocity, that is, the measured object velocity. The calculator 7 outputs the velocity data to the DSC 9.

Preferably, an ultrasound pulse beam is repetitively emitted in a same direction a plurality of times. In this case, a related ultrasound echo beam coming along the direction is repetitively received the plurality of times, and velocity data are generated the plurality of times. The calculator 7 stores each of the plural-time velocity data into the memory 8. The calculator 7 reads the plural-time velocity data from the memory 8. The calculator 7 averages the plural-time velocity data into mean velocity data. The calculator 7 outputs the mean velocity data to the DSC 9 instead of the non-average velocity data.

The calculator 7 stores the velocity data (the non-average velocity data or the mean velocity data) into the memory 8 for later use as previous velocity data. The calculator 7 computes the distance traveled by the object on the basis of the present velocity data (the present non-average velocity data or the present mean velocity data) and the previous velocity data read out from the memory 8. The calculator 7 generates data (traveled-distance data) representing the computed distance traveled by the object. The calculator 7 outputs the traveled-distance data to the DSC 9.

Under the control by the CPU 11, the DSC 9 subjects the output data from the calculator 7 to scan conversion, and thereby converts the data into a video signal of a given format suited for indication on the monitor 12. The DSC 9 outputs the video signal to the display controller 10.

In the case where the blood pressure detector 15 and the ECG 16 are connected to the display controller 10, the blood pressure detector 15 and the ECG 16 output signals to the display controller 10 which represent a blood pressure waveform and an electrocardiogram respectively. Under the control by the CPU 11, the display controller 10 converts the output signals of the blood pressure detector 15 and the ECG 16 into video signals of the given format suited for indication on the monitor 12. The display controller 10 superimposes these video signals on the video signal outputted from the DSC 9. The display controller 10 outputs the superimposition-resultant video signal to the monitor 12. The monitor 12 visualizes and indicates the output signal of the display controller 10. Thus, the velocity of the object, the distance traveled by the object, the blood pressure waveform, and the electrocardiogram are displayed on the monitor 12.

The ultrasound diagnostic apparatus implements the measurement of the velocity of an object or the velocities of objects in one of first, second, third, fourth, and fifth methods mentioned hereinafter.

According to the first measurement method, as shown in FIG. 2, a direction perpendicular to the front surface of the ultrasound probe 1 is defined as an "x" direction while a direction parallel to the front surface of the ultrasound probe 1 is defined as a "z" direction. The velocity of an object OB is measured by using emitted and received ultrasound beams in an acoustic line direction #1 equal to the "x" direction. The measured object velocity is denoted by Vx. The acoustic line of the direction #1 meets the object OB. In addition, the velocity of the object OB is measured by using emitted and received ultrasound beams in an acoustic line direction #2 which deflects from the acoustic line direction #1 by a given angle θ. The measured object velocity is denoted by V'. The acoustic line of the direction #2 meets the object OB. In the case where the object OB is moving only in the "x" direction, the measured object velocity V' regarding the acoustic line direction #2 and the measured object velocity Vx regarding the acoustic line direction #1 are in the following relation.

$$V' = Vx \cdot \cos \theta \quad (1)$$

On the other hand, in the case where the motion of the object OB has a nonzero "z"-direction component, the measured object velocities V' and Vx are in the following relation.

$$V' > Vx \cdot \cos \theta \quad (2)$$

For example, the calculator 7 decides which of the relations (1) and (2) is satisfied. When the relation (1) is satisfied, it is determined that the object OB is moving only in the "x" direction. In this case, the measured object velocity Vx is used as an actual measured object velocity. When the relation (2) is satisfied, it is determined that the direction of motion of the object OB has a nonzero "z"-direction component. In this case, the measured object velocity V' is greater than the value "Vx·cos θ" by a quantity which increases as the "z"-direction component of the object motion increases. The object velocity Vz in the "z" direction is estimated or calculated from the difference between the measured object velocity V' and the value "Vx·cos θ". An actual measured object velocity (that is, a velocity of an object in a direction of motion thereof) V is calculated from the object velocity Vx and the object velocity Vz. In addition, an actual direction of motion of the object is calculated from the object velocity Vx and the object velocity Vz. According to the first measurement method, the velocity of an object OB may be repetitively measured by using emitted and received ultrasound beams in three or more different acoustic line directions.

Figure 3:
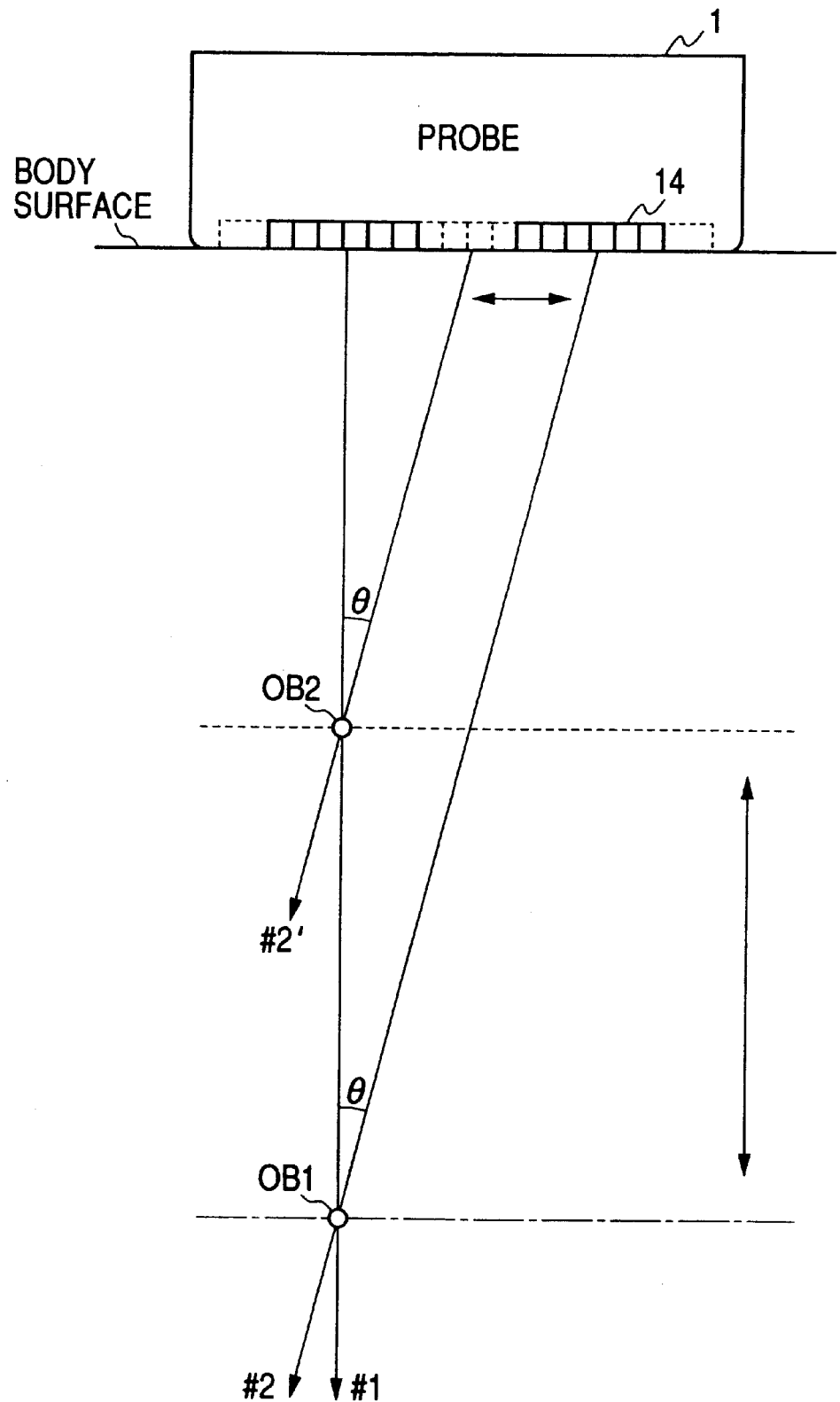
FIG. 3 is a diagram of an ultrasound probe, acoustic line directions, and objects.

According to the second measurement method, as shown in FIG. 3, the velocity of an object OB1 and the velocity of an object OB2 are measured by using emitted and received ultrasound beams in an acoustic line direction #1 equal to the "x" direction. The objects OB1 and OB2 align in the "x" direction. The acoustic line of the direction #1 meets the objects OB1 and OB2. The position of the object OB1 is deeper than the position of the object OB2 with respect to the body surface. In addition, the velocity of the object OB1 is measured by using emitted and received ultrasound beams in an acoustic line direction #2 which deflects from the acoustic line direction #1 by a given angle θ. The acoustic line of the direction #2 meets the object OB1. Furthermore, the velocity of the object OB2 is measured by using emitted and received ultrasound beams in an acoustic line direction #2' parallel to and separate from the acoustic line direction #2. The acoustic line of the direction #2' meets the object OB2. The acoustic line directions #2 and #2' are equal in deflection angle relative to the acoustic line direction #1. An actual measured velocity of the object OB1, and an actual direction of motion of the object OB1 are calculated as in the first measurement method. Similarly, an actual measured velocity of the object OB2, and an actual direction of motion of the object OB2 are calculated as in the first measurement method. The emitted and received ultrasound beams in the acoustic line direction #2 or the acoustic line direction #2' are provided by steps including a step of selecting piezoelectric elements from the piezoelectric-element array 14 as a group of actively-used piezoelectric elements. The replacement of the emitted and received ultrasound beams in the acoustic line direction #2 by those in the acoustic line direction #2' is implemented by shifting the group of actively-used piezoelectric elements relative to the piezoelectric-element array 14 while holding unchanged the signal delays related to the actively-used piezoelectric elements. According to the second measurement method, the velocities of three or more objects at different depths may be measured.

Figure 4:
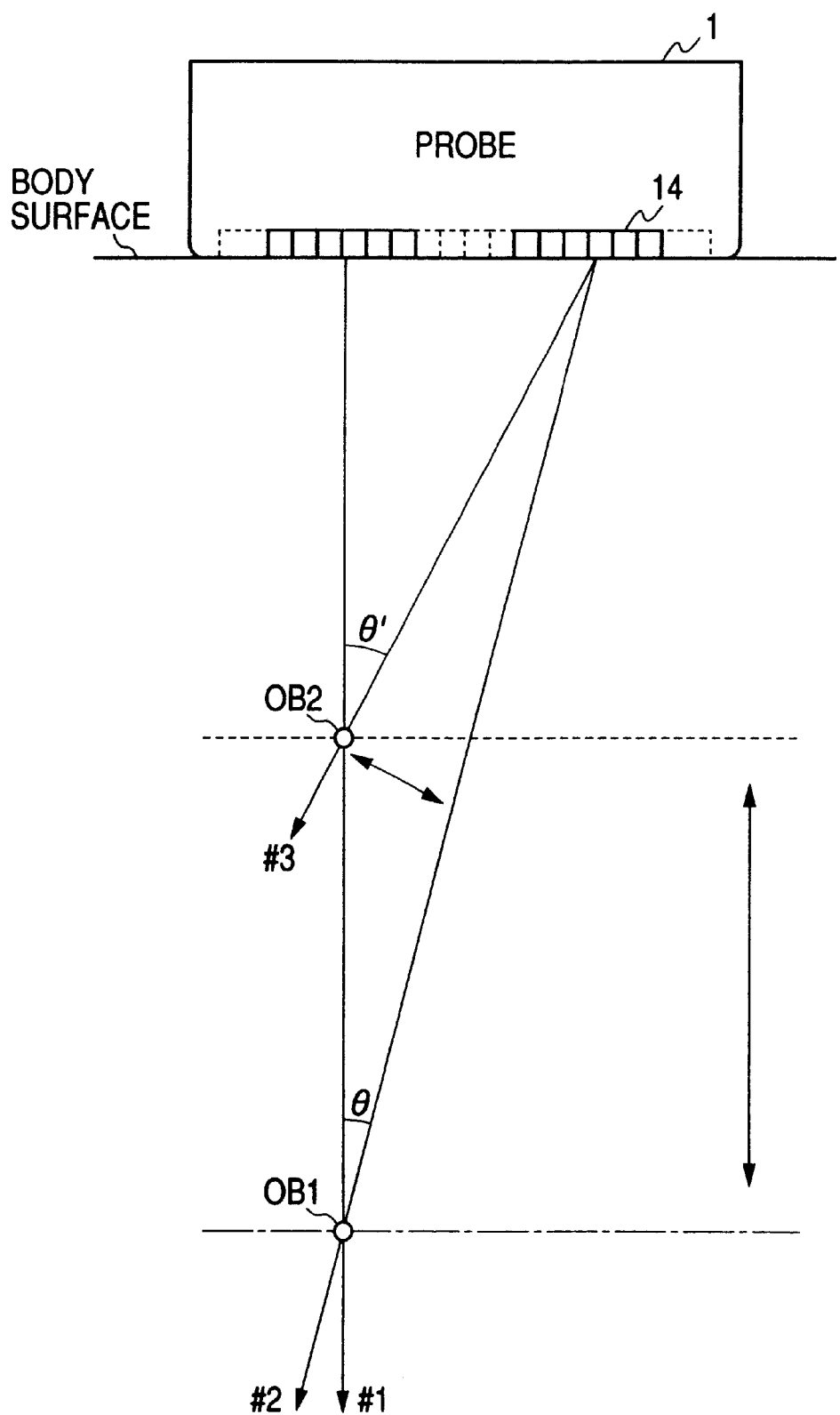
FIG. 4 is a diagram of an ultrasound probe, acoustic line directions, and objects.

According to the third measurement method, as shown in FIG. 4, the velocity of an object OB1 and the velocity of an object OB2 are measured by using emitted and received ultrasound beams in an acoustic line direction #1 equal to the "x" direction. The objects OB1 and OB2 align in the "x" direction. The acoustic line of the direction #1 meets the objects OB1 and OB2. The position of the object OB1 is deeper than the position of the object OB2 with respect to the body surface. In addition, the velocity of the object OB1 is measured by using emitted and received ultrasound beams in an acoustic line direction #2 which deflects from the acoustic line direction #1 by a given angle θ. The acoustic line of the direction #2 meets the object OB1. Furthermore, the velocity of the object OB2 is measured by using emitted and received ultrasound beams in an acoustic line direction #3 which deflects from the acoustic line direction #1 by a given angle θ' different from the given angle θ. The acoustic line of the direction #3 meets the object OB2. An actual measured velocity of the object OB1, and an actual direction of motion of the object OB1 are calculated as in the first measurement method. Similarly, an actual measured velocity of the object OB2, and an actual direction of motion of the object OB2 are calculated as in the first measurement method. The emitted and received ultrasound beams in the acoustic line direction #2 or the acoustic line direction #3 are provided by steps including a step of selecting piezoelectric elements from the piezoelectric-element array 14 as a group of actively-used piezoelectric elements. The replacement of the emitted and received ultrasound beams in the acoustic line direction #2 by those in the acoustic line direction #3 is implemented by controlling or changing the signal delays related to the actively-used piezoelectric elements without changing the selection of the actively-used piezoelectric elements. According to the third measurement method, the velocities of three or more objects at different depths may be measured.

The fourth measurement method is similar to one of the first, second, and third measurement methods except for design changes mentioned hereinafter. With reference to FIG. 2, the previously-mentioned relation (2) is changed into a general equation as follows.

$$V' = (Vx + A) \cdot \cos \theta \tag{3}$$

where "A" denotes a value defined along the "x" direction (the acoustic line direction #1) and related to a "z"-direction component of the motion of the object OB. The value "A" is different from 0 when a nonzero "z"-direction component is present in the motion of the object OB. The value "A" is equal to 0 when a nonzero "z"-direction component is absent from the motion of the object OB. The equation (3) is changed into the following equations.

$$Vx + A = V'/\cos \theta \tag{4}$$

$$A = (V'/\cos \theta) - Vx \tag{5}$$

As shown in FIG. 2, the value "A", the angle θ, and the object velocity Vz in the "z" direction are in the following relation.

$$A = Vz \cdot \tan \theta \tag{6}$$

Combining the equation (5) and the relation (6) results in an equation as follows.

$$Vz = (1/\sin \theta) \cdot (V' - Vx \cdot \cos \theta) \tag{7}$$

The object velocity Vz in the "z" direction is calculated from the measured object velocities Vx and V', and the angle θ by using the equation (7). An actual measured object velocity V is calculated from the "x"-direction object velocity Vx and the "z"-direction object velocity Vz in accordance with the following equation.

$$V = (Vx^2 + Vz^2)^{1/2} \tag{8}$$

The angle θv of the direction of motion of the object OB relative to the front surface of the ultrasound probe 1 is calculated from the "x"-direction object velocity Vx and the "z"-direction object velocity Vz by using an equation as follows.

$$\theta v = \tan^{-1}(Vz/Vx) \tag{9}$$

It should be noted that the object velocity Vx regarding the acoustic line direction #1 and the object velocity V' regarding the acoustic line direction #2 may be detected by an FFT Doppler technique. The body to be examined may be scanned by an ultrasound beam to spatially detect the rate and direction of motion.

Figure 5:
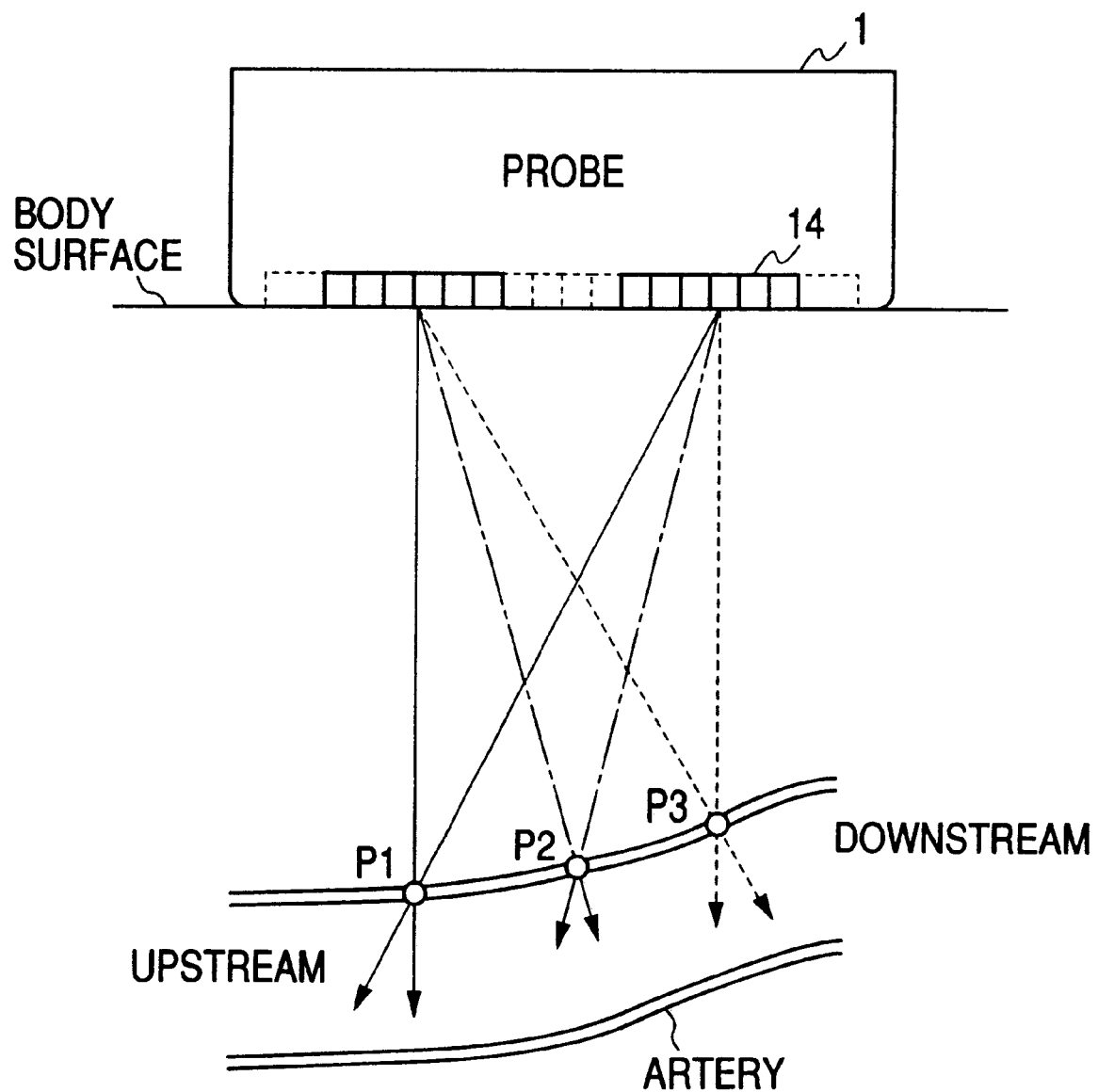
FIG. 5 is a diagram of an ultrasound probe, acoustic line directions, measurement points, and curved arterial walls.

The fifth measurement method is similar to one of the first, second, third, and fourth measurement methods except for design changes mentioned hereinafter. The fifth measurement method is suited for detection of motion parameters of arterial walls which curve relative to the surface of the body, that is, the front surface of the ultrasound probe 1. According to the fifth measurement method, a B-mode image (a sectional image) of the body is indicated on the monitor 12. With reference to FIG. 5, an image of arterial walls in the B-mode image of the body is traced, and spaced measurement points P1, P2, and P3 are defined on the image of the arterial walls. Transmission delay control data for enabling the ultrasound pulse beams to hit the measurement points P1, P2, and P3 are individually calculated. For each of the measurement points P1, P2, and P3, the calculated transmission delay control data correspond to ultrasound pulse beams in two different acoustic line directions. Reception delay control data for sensitively catching the ultrasound echo beams coming from the measurement points P1, P2, and P3 are individually calculated. The calculated transmission delay control data and the calculated reception delay control data are stored in the memory 4. The delay controller 3 reads the transmission delay control data from the memory 4, and controls the delays of the electric drive pulse signals in accordance with the transmission delay control data. Thus, the measurement points P1, P2, and P3 are sequentially hit by the ultrasound pulse beams. The delay controller 3 reads the reception delay control data from the memory 4, and controls the delays of the electric echo signals in accordance with the reception delay control data. Thus, the ultrasound echo beams coming from the measurement points P1, P2, and P3 are sequentially received. Velocities of each of the measurement points P1, P2, and P3 regarding two different acoustic line directions are measured as in the fourth measurement method. The measured velocities of the measurement points P1, P2, and P3 are indicated on the monitor 12 as a waveform. Thereby, it is possible to easily grasp motion of the arterial walls along the direction of a normal and also motion thereof along the direction of a tangent. Furthermore, the velocity of each of the measurement points P1, P2, and P3 along the direction of a normal and the velocity thereof along the direction of a tangent may be calculated. In this case, the calculated velocities of the measurement points P1, P2, and P3 are indicated on the monitor 12.

The ultrasound diagnostic apparatus implements the indication of the measurement results on the monitor 12 in one of first, second, third, and fourth methods mentioned hereinafter.

Figure 6:
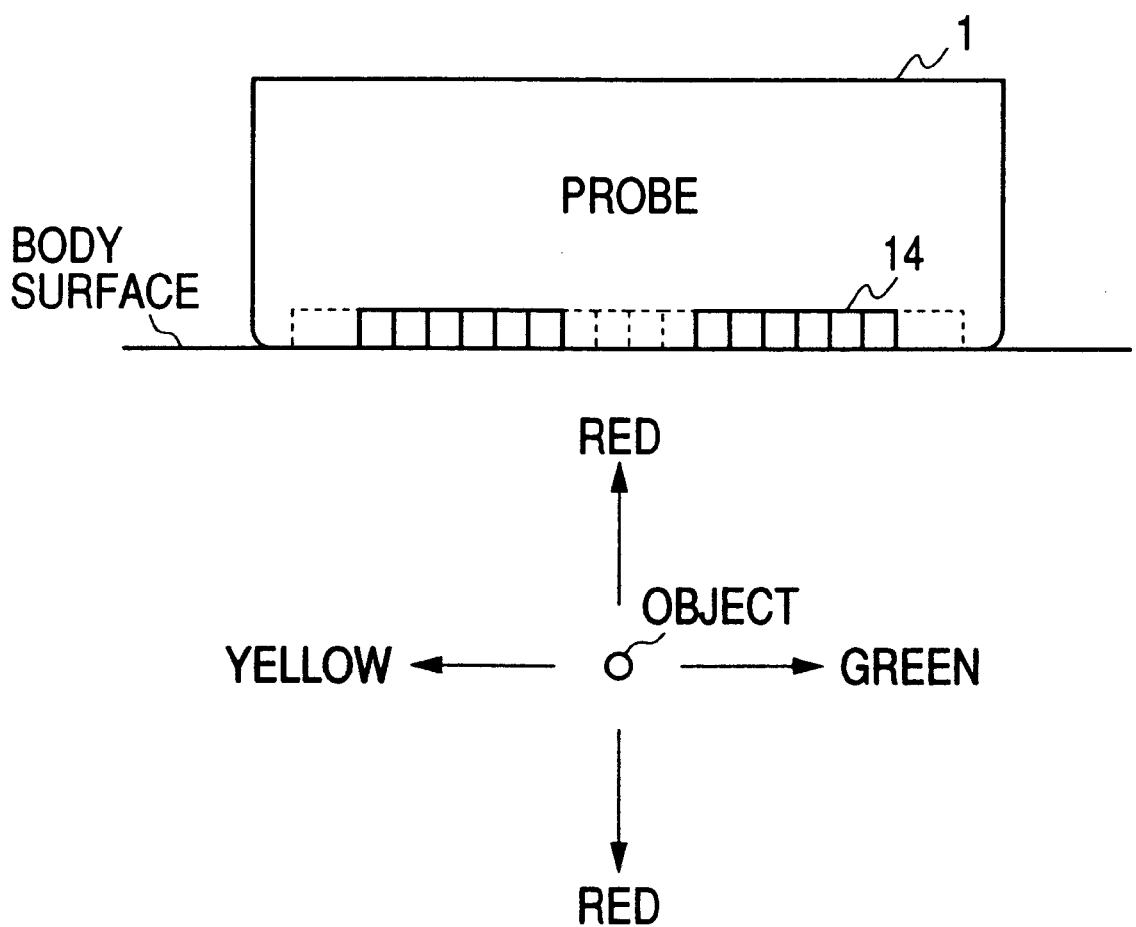
FIG. 6 is a diagram of an ultrasound probe, an object, and a color of indication of the object.

The first indication method is applied to the measurement results provided in the fourth measurement method. Specifically, the velocity of a tissue (or an organ) in the body along a direction perpendicular to the front surface of the ultrasound probe 1, and also the velocity of the tissue (or the organ) along a direction parallel to the front surface of the ultrasound probe 1 are two-dimensionally measured in the fourth measurement method while the body is scanned by the ultrasound pulse beam. The measurement results are indicated on the monitor 12 as a color distribution superimposed over the B-mode image of the body. In addition, the distance traveled by the tissue (or the organ) along the direction perpendicular to the front surface of the ultrasound probe 1, and also the distance traveled by the tissue (or the organ) along the direction parallel to the front surface of the ultrasound probe 1 are calculated while the body is scanned by the ultrasound pulse beam. The calculation results are indicated on the monitor 12 as a color distribution superimposed over the B-mode image of the body. Thereby, it is possible to easily grasp motion of a local place in the tissue (or the organ). According to the first indication method, as shown in FIG. 6, an object is indicated by a red region when the object is moving toward the ultrasound probe 1. The tone of the red is increased as the measured velocity of the object rises. An object is indicated by a blue region when the object is moving away from the ultrasound probe 1. The tone of the blue is increased as the measured velocity of the object rises. An object is indicated by a green region when the object is moving in one direction (for example, the rightward direction as viewed in FIG. 6) parallel to the front surface of the ultrasound probe 1. The tone of the green is increased as the measured velocity of the object rises. An object is indicated by a yellow region when the object is moving in the other direction (for example, the leftward direction as viewed in FIG. 6) parallel to the front surface of the ultrasound probe 1. The tone of the yellow is increased as the measured velocity of the object rises. When an object is moving in a direction intermediate between the upward direction and the rightward direction as viewed in FIG. 6, the object is indicated by a region having a color intermediate between red and green. It should be noted that red, blue, green, and yellow may be replaced by other colors. Used colors may be freely selected by a user.

Figure 7:
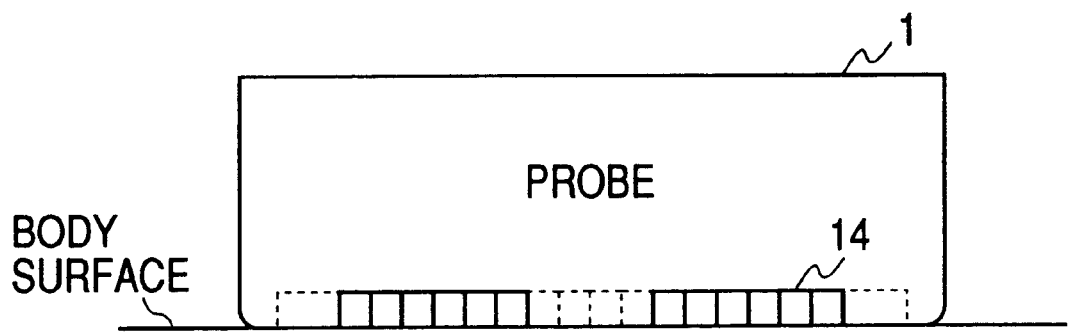
FIG. 7 is a diagram of an ultrasound probe, measurement points, arterial walls, and colors of indication of the measurement points.
Figure 7:
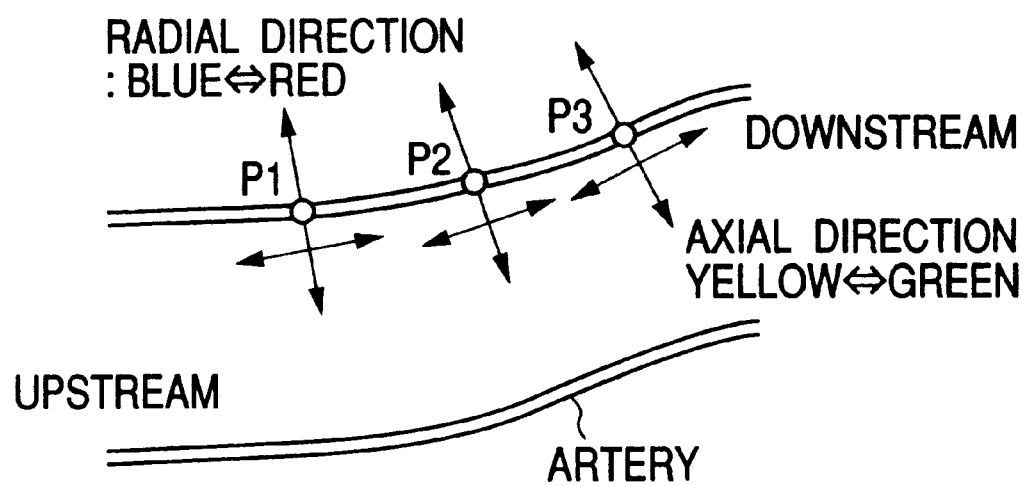

The second indication method is applied to the measurement results provided in the fifth measurement method. According to the second indication method, the velocity of arterial walls along the direction of a normal and also the velocity thereof along the direction of a tangent are indicated on the monitor 12 as two-dimensional color distributions superimposed over the B-mode image of the body. In addition, the distance traveled by the arterial walls along the direction of the normal and also the distance traveled thereby along the direction of the tangent are indicated on the monitor 12 as two-dimensional color distributions superimposed over the B-mode image of the body. Thereby, it is possible to easily grasp motion of the arterial walls which is caused by a heartbeat. As shown in FIG. 7, each measurement point (P1, P2, or P3) on the arterial walls is indicated by a red region when the measurement point is moving in a radially inward direction (one direction of a normal). The tone of the red is increased as the velocity of the measurement point rises. Each measurement point (P1, P2, or P3) on the arterial walls is indicated by a blue region when the measurement point is moving in a radially outward direction (the other direction of the normal). The tone of the blue is increased as the velocity of the measurement point rises. Each measurement point (P1, P2, or P3) on the arterial walls is indicated by a green region when the measurement point is moving in one axial direction (one direction of a tangent). The tone of the green is increased as the velocity of the measurement point rises. Each measurement point (P1, P2, or P3) on the arterial walls is indicated by a yellow region when the measurement point is moving in the other axial direction (the other direction of the tangent). The tone of the yellow is increased as the velocity of the measurement point rises. It should be noted that red, blue, green, and yellow may be replaced by other colors. Used colors may be freely selected by a user.

The third indication method is similar to the first indication method (or the second indication method) except for design changes mentioned hereinafter. According to the third indication method, the blood pressure waveform and the electrocardiogram are displayed on the monitor 12 while being superimposed over the B-mode image of the body and the two-dimensional color distributions of the velocity of a tissue (or an organ) and the distance traveled by the tissue (or the organ). The superimposition is on a real-time basis. Thereby, it is possible to easily grasp motion of the tissue (or the organ) which is caused by a heartbeat.

The fourth indication method is similar to the second indication method (or the first indication method) except for design changes mentioned hereinafter. According to the fourth indication method, the blood pressure waveform and the electrocardiogram are displayed on the monitor 12 while being superimposed over the B-mode image of the body and the two-dimensional color distributions of the velocities of measurement points on arterial walls along the direction of a normal, the velocities of the measurement points along the direction of a tangent, the distances traveled by the measurement points along the direction of the normal, and the distances traveled by the measurement points along the direction of the tangent. The superimposition is on a real-time basis. Thereby, it is possible to easily grasp heartbeat-caused motion of the arterial walls along the direction of the normal and also heartbeat-caused motion thereof along the direction of the tangent.

What is claimed is:

1. An ultrasound diagnostic apparatus comprising:

transmitting means including an ultrasound probe for transmitting a ultrasound pulse beam from the ultrasound probe into a body;

receiving means including the ultrasound probe for receiving an ultrasound echo beam caused in the body, and converting the received ultrasound echo beam into a corresponding electric echo signal via the ultrasound probe;

delay controlling means for controlling an acoustic line direction of transmission and reception of the ultrasound pulse beam and the ultrasound echo beam;

phase detection means for subjecting the electric echo signal to phase detection to generate a phase-detection result signal;

tissue velocity calculating means for calculating a velocity of a tissue in the body from the phase-detection result signal; and display means for indicating the calculated velocity of the tissue;

wherein the delay controlling means comprises means for changing the acoustic line direction of transmission and reception of the ultrasound pulse beam and the ultrasound echo beam with respect to a same object.

2. An ultrasound diagnostic apparatus as recited in claim 1, wherein the ultrasound probe includes transducer elements, and further comprising means for selecting ones from among the transducer elements as active elements in response to a depth of a measured portion of the tissue from a surface of the body.

3. An ultrasound diagnostic apparatus as recited in claim 1, wherein the delay controlling means comprises means for changing the acoustic line direction of transmission and reception of the ultrasound pulse beam and the ultrasound echo beam in response to a depth of a measured portion of the tissue from a surface of the body.

4. An ultrasound diagnostic apparatus as recited in claim 1, wherein the delay controlling means comprises means for changing the acoustic line direction of transmission and reception of the ultrasound pulse beam and the ultrasound echo beam among a plurality of different directions with respect to the tissue, and the tissue velocity calculating means comprises means for calculating a velocity of the tissue in a direction perpendicular to a front surface of the ultrasound probe, a distance traveled by the tissue in the direction perpendicular to the front surface of the ultrasound probe, a velocity of the tissue in a direction parallel to the front surface of the ultrasound probe, and a distance traveled by the tissue in the direction parallel to the front surface of the ultrasound probe from the phase-detection result signal.

5. An ultrasound diagnostic apparatus as recited in claim 1, wherein the delay controlling means comprises means for changing the acoustic line direction of transmission and reception of the ultrasound pulse beam and the ultrasound echo beam to scan arterial walls in the body, the tissue velocity calculating means comprises means for calculating a velocity of the arterial walls in a direction of a normal, a distance traveled by the arterial walls in the direction of the normal, a velocity of the arterial walls in a direction of a tangent, and a distance traveled by the arterial walls in the direction of the tangent from the phase-detection result signal, and the display means comprises means for indicating the calculated velocity of the arterial walls in the direction of the normal, the calculated distance traveled by the arterial walls in the direction of the normal, the calculated velocity of the arterial walls in the direction of the tangent, and the calculated distance traveled by the arterial walls in the direction of the tangent as waveforms.

6. An ultrasound diagnostic apparatus as recited in claim 4, wherein the display means comprises means for indicating a B-mode image of the body, and means for indicating the calculated velocity of the tissue in the direction perpendicular to the front surface of the ultrasound probe, the calculated distance traveled by the tissue in the direction perpendicular to the front surface of the ultrasound probe, the calculated velocity of the tissue in the direction parallel to the front surface of the ultrasound probe, and the calculated distance traveled by the tissue in the direction parallel to the front surface of the ultrasound probe as two-dimensional color distributions superimposed over the B-mode image of the body.

7. An ultrasound diagnostic apparatus as recited in claim 5, wherein the display means comprises means for indicating a B-mode image of the body, and means for indicating the calculated velocity of the arterial walls in the direction of the normal, the calculated distance traveled by the arterial walls in the direction of the normal, the calculated velocity of the arterial walls in the direction of the tangent, and the calculated distance traveled by the arterial walls in the direction of the tangent as two-dimensional color distributions superimposed over the B-mode image of the body.

8. An ultrasound diagnostic apparatus as recited in claim 6, wherein the display means comprises means for indicating a blood pressure waveform and an electrocardiogram superimposed over the B-mode image of the body and the two-dimensional color distributions.

9. An ultrasound diagnostic apparatus as recited in claim 7, wherein the display means comprises means for indicating a blood pressure waveform and an electrocardiogram superimposed over the B-mode image of the body and the two-dimensional color distributions.

10. An ultrasound diagnostic apparatus comprising:
first means for transmitting a first ultrasound pulse beam into a body toward an object within the body along a first direction;
second means for receiving a first ultrasound echo beam caused by reflection of the first ultrasound pulse beam at the object and coming from the object along the first direction;
third means for transmitting a second ultrasound pulse beam into the body toward the object within the body along a second direction angularly different from the first direction;
fourth means for receiving a second ultrasound echo beam caused by reflection of the second ultrasound pulse beam at the object and coming from the object along the second direction;
fifth means for calculating a velocity of the object along the first direction from the first ultrasound echo beam received by the second means; and
sixth means for calculating a velocity of the object along the second direction from the second ultrasound echo beam received by the fourth means.

11. An ultrasound diagnostic apparatus as recited in claim 10, wherein the first direction is perpendicular to a surface of the body, and further comprising seventh means for calculating a velocity of the object along a third direction parallel to the surface of the body from the velocity calculated by the fifth means, the velocity calculated by the sixth means, and an angular difference between the first direction and the second direction.

12. An ultrasound diagnostic apparatus as recited in claim 10, further comprising seventh means for calculating a direction of motion of the object from the velocity calculated by the fifth means, the velocity calculated by the sixth means, and an angular difference between the first direction and the second direction, and eighth means for calculating a velocity of the object along the calculated direction of motion of the object from the velocity calculated by the fifth means, the velocity calculated by the sixth means, and the angular difference between the first direction and the second direction.

* * * * *